United States Patent [19]

Belzecki et al.

[11] 3,953,512

[45] Apr. 27, 1976

[54] PROCESS FOR MANUFACTURING 2-AMINOBUTANOL

[75] Inventors: Czeslaw Belzecki; Witold Tomasik; Jerzy Trojnar, all of Warsaw, Poland

[73] Assignee: Polska Akademia Nauk Instytut Chemii Organicznej, Warsaw, Poland

[22] Filed: Mar. 18, 1974

[21] Appl. No.: 452,372

[30] Foreign Application Priority Data

Mar. 20, 1973 Poland .................................. 161371

[52] U.S. Cl. ............................................ 260/584 R
[51] Int. Cl.² .................. C07C 91/02; C07C 93/02; C07C 93/10; C07C 95/02
[58] Field of Search .............................. 260/584 R

[56] References Cited
UNITED STATES PATENTS

| | | | |
|---|---|---|---|
| 3,325,476 | 6/1967 | DowBenko | 260/584 R X |
| 3,448,153 | 6/1969 | Cavitt et al. | 260/584 R |
| 3,660,488 | 5/1972 | Cobb | 260/584 R |

Primary Examiner—Paul F. Shaver
Attorney, Agent, or Firm—Haseltine, Lake & Waters

[57] ABSTRACT

The invention relates to a method of preparation of 2-aminobutanol from readily available raw materials. The method of this invention is based on the reaction between 1.2-epoxybutane or isomeric butylene halogenehydrines with ammonia. The product, isomeric aminobutanols, are, subsequently transformed into 2-ethylaziridine by means of esterification with sulphuric acid followed by treatment with alkali. 2-Ethylaziridine is then submitted to a reaction with aromatic carboxylic acid or with aromatic orthobicarboxylic acid anhydride which produces the corresponding monomeric or polymeric amide, which is transformed into 2-aminobutanol by hydrolysis.

The method of this invention is a multistage one but is quite simple and employs aqueous solutions and organic solvents, such as chloroform or benzene, which may be easily recovered.

5 Claims, 1 Drawing Figure

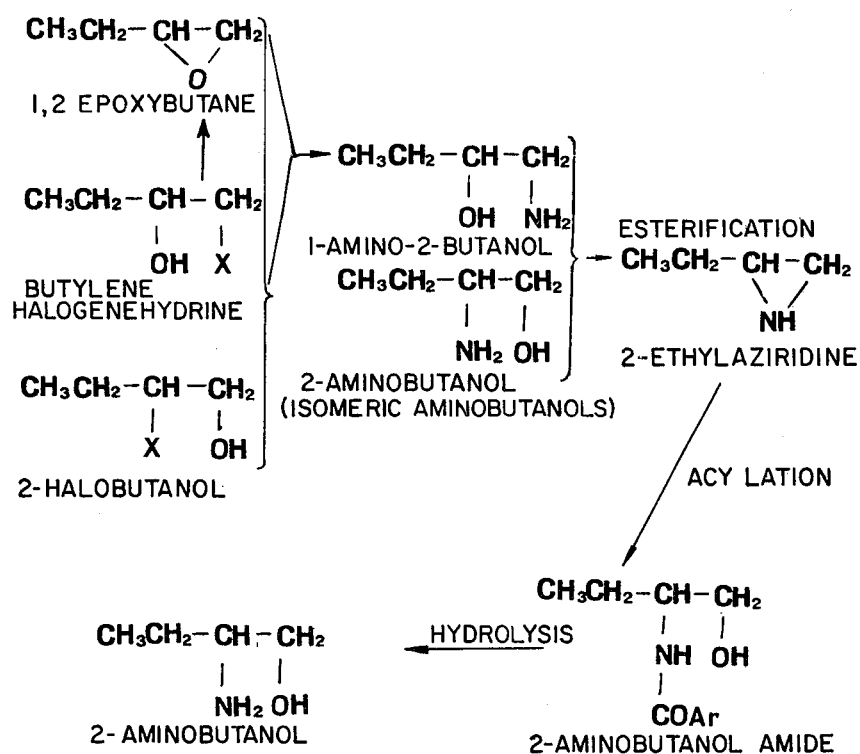
(FLOW SHEET)

PROCESS FOR MANUFACTURING 2-AMINOBUTANOL

The invention relates to a process of preparation of 2-aminobutanol used as an intermediate for the production of biologically active butanol derivatives.

A known method of preparation 2-aminobutanol is based upon a condensation of 1-nitropropane with formaldehyde and subsequent reduction of 2-nitrobutanol. The method is technologically easy but 1-nitropropane used for the reaction is obtained by nitration of paraffins. The nitration process, however, leads to a series of nitroparaffines which are very difficult to separate.

Another method of 2-aminobutanol preparation comprises reduction of 2-propyl-3-nitroso-4-ethyloxazolidine, reduction of amino-butyric acid esters and hydrogenolytic splitting of N-benzylo-aminobutanol.

The above methods, unfortunately, cannot be employed to a full technological extent because the raw materials and reagents used in the process are not commercially available. Accordingly, the methods have only laboratory significance.

The object of this invention is to provide a manufacturing method for making 2-aminobutanol in simple technological operations using cheap and easily available raw materials.

It was found that 2-aminobutanol can be obtained by reacting 1,2-epoxybutane, or alternatively, butylene halogen hydrines, obtained in a known process from 1-butene, with ammonia. The resulting mixture of isomeric aminobutanols was then transformed into 2-ethyl aziridine by esterification with sulphuric acid with subsequent treatment with alkali. 2-Ethylaziridine was then acylated with an aromatic carboxylic acid or with an orthobicarboxylic acid anhydride. The 2-aminobutanolamide or the polymeric amide of 2-aminobutanol produced thereby, was then hydrolysed with a mineral acid.

The method of this invention is presented graphically in the accompanying flow sheet, where X-is a halogen and Ar- is an aryl.

According to the method outlined in the flow sheet, 1,2-epoxybutane, or alternatively, of butylene halogen-hydrines i.e. 1-hydroxy-2-halogenbutane and 1-halogen-2-hydroxybutane is reacted with ammonia, advantageously in aqueous solution with an excess of ammonia. When butylene halogen hydrines are used as the starting materials, according to a known mechanism of the reaction, an intermediate 1.2-epoxybutane is formed. Upon addition of an excess of the reagent, a mixture of isomeric aminobutanoles are formed, in which 1-amino-2-butanol predominates over 2-aminobutanol. Such a mixture cannot be separated by fractional distillation or crystallization of simple salts. Accordingly, the mixture is transformed directly into 2-ethylaziridine by means of an esterification of hydroxy groups with sulphuric acid, followed by intramolecular alkylation of amine groups in an alkaline medium, preferably in a solution of alkaline hydroxide.

The 2-Ethylaziridine is then transformed into the corresponding 2-aminobutanol via the 2-aminobutanol amide, by acid hydrolysis. Depending upon the nature of the acid medium used, for formation of the amide, either monomeric or polymeric amides are obtained. An aromatic carboxylic acid, such as benzoic acid, or, alternatively, an orthobicarboxylic acid anhydride, such as phthalic anhydride, may be used in the reaction.

The last step of the process is the hydrolysis of the 2-aminobutanol amide using a mineral acid, preferably hydrochloric acid. The aromatic acid obtained as a result of hydrolysis can be removed from the reaction mixture by means of distillation or filtration.

The method of the invention is a multistage one but is quite simple. It is conducted in aqueous or organic solvents, such as chloroform or benzene, which can be easily recovered. The process is carried out in a simple apparatus, and under conditions where neither high temperatures nor high pressures are necessary.

The starting materials and reactants in the process are generally readily available or can be easily obtained by known processes. Thus, butylene halogen hydrines can be obtained from 1-butene by means of a reaction with alkalimetal hypochlorites or alkaline earth metals hypochlorites, or bromine in aqueous sodium or potassium bromide, or N-bromosuccinimide or, by means of reaction with N-halogenamines, such as N-chloroamine or N-chloroamide, or by means of a reaction with organic hypochlorites, such as t-butylhypochlorite.

The preparation of 1.2-epoxybutene is also not difficult and may be performed by reacting butylene halogenhydrines with alkali metals hydroxides or by catalytic oxidation of butene-1.

The method is illustrated in the following examples which do not limit, whatsoever, the scope of the invention.

EXAMPLE 1

74 g of 1.2-epoxybutane was dissolved in 2.0 ltrs of 25 per cent aqueous solution of ammonia and left for 3 days at room temperature. Thereafter, an excess of ammonia was distilled off normal pressure using a 30 cms long distillation column. The distillation was continued until a temperature of 100°–102°C was reached. After that, it was conducted under reduced pressure. After having removed a small fore run, the main fraction between 74°C and 78°C at 12 mm Hg was collected. The product contained water which was removed with solid potassium hydroxide. The fraction obtained was then redistilled and collected. The yield was 65–70 per cent. The product is a mixture of 1-amino-2-butanol and 2-aminobutanol with a substantial excess of the former.

89 g of the mixture of isomeric aminobutanols, obtained according to the method as above, was dissolved in 400 ccm of toluene, cooled, and to the solution 98 of concentrated sulfuric acid was added while cooling.

The mixture was transferred to a distillation apparatus provided with an azeotropic distillation head and an azeotropic water-toluene mixture was distilled off. The reaction was conducted until 17 cc. of water was collected in azeotropic head recipient. Toluene was then evaporated off in a rotary evaporator and to the remaining mixture 400 ccm of water was added and, while cooling, a 50 per cent aqueous solution of potassium hydroxide prepared from 230 g KOH, was added. The mixture was then transferred into a distillation apparatus provided with a distillation column of 40 cms. The distillation was carried on until a temperature of 100°C was reached. To the distillate solid potassium hydroxide was added in a quantity sufficient to obtain a visible separation of the layers. The organic layer was separated, distilled, dried and redistilled. 40 g 2-Ethylaziridine was obtained, which corresponds to a yield of 56 per cent.

To 7.1 g 2-Ethylaziridine, obtained according to the method described above, dissolved in 50 cc chloroform were added 14.8 g of finely ground phthalic anhydride and the mixture was heated during 3 hours. The mixture was then evaporated on a rotary evaporiser. The remaining mass was an amorphous polyamide.

The polyamide was treated with 100 cc of 20 per cent hydrochloric acid and heated for 4 hours until the boiling point was reached. The mixture was cooled down and about 16 g of phthalic acid was filtered off.

To the filtrate 30 per cent solution of sodium hydroxide was added and the mixture extracted several times with benzene. The benzene extracts were joined, dried over solid potassium hydroxide, and benzene evaporated. The remainder was distilled under reduced pressure to obtain 4.5 g of 2-aminobutanol which quantity corresponds to a 50 per cent yield.

EXAMPLE 2

To 58 g of benzoic acid dissolved in 500 cc of chloroform 10.6 g of ethylaziridine, obtained according to the method described in Example 1, was added. The mixture was heated under reflux during 2 hours, and left for 2 days in a room temperature. The mixture was then poured over a saturated aqueous solution of sodium bicarbonate, mixed and separated. The organic layer was shaked twice with aqueous solution of sodium bicarbonate, dried and the solvent was evaporated. To the remainder 100 cc of benzene was added and the mixture left for a couple of hours. The amide crystals were then filtered off and washed with small portions of benzene. The filtrate was concentrated by evaporation to half its original volume. The concentrated filtrate was left for crystallization in order to separate a further portion of the amide. Some petroleum ether was added to the filtrate to a turbid condition, and the mixture was left to crystallize more of the amide. A total of 20 g of N-benzoyl-2-aminobutanol were obtained.

The purity of amide was determined by means of thin-layer chromatography using silica-gel with a luminophor. The chromatgrammes were developed with a mixture benzene: ether = 1:4 and observed in UV light.

The amide obtained in the procedure described above was mixed with 150 g of 30 per cent hydrochloric acid and refluxed during 4 hours. Benzoic acid which evolved in the process was distilled off with water steam. The cooled remaining mixture was then neutralised with 20 per cent aqueous solution of sodium hydroxide and extracted several times with other. The other layer was then dried and the ether evaporated. The remaining liquid was distilled under reduced pressure and a fraction of 75°–77°C (at 10–12 mm Hg) was collected. The yield was 7.6 g of 2-aminobutanol which corresponds to a 61 per cent based upon 2-ethylaziridine and 85 per cent calculated based upon the amide.

2-Ethylaziridine was obtained according to the process presented in Example 1, or in the following manner: To 89 g of a mixture of isomeric aminobutanols, wherein the content ratio of 2-aminobutanol to 1-amino-2-butanol is not significant, about 75 ml of 50 per cent of an aqueous solution of sulphuric acid was added while cooling and stirring to obtain a solution neutral in the presence of methyl orange indicator. A similar portion of 50 per cent acid was added and the mixture was evaporated under reduced pressure in a rotative vaporiser to obtain dry sediment. After grinding, the sediment was dried to a constant weight.

To a cooled solution of the sulphate in 400 ccm of water, a solution of 200 g of potassium hydroxide in 200 ccm water were added dropwise under stirring and cooling. The mixture was then transferred to a distillation apparatus provided with a 400 mm distillation column and gradually heated. After certain lapse of time crystalline potassium sulphate precipitated and, at about 85°C, the product started to distill. Distillation was carried until a temperature of 100°C. To the distillate solid potassium hydroxide was added in a quantity sufficient to obtain a separation of the layers. The organic layer was separated, dried over solid potassium hydroxide and re-distilled; yield about 60 g (85 per cent) - Boiling point 89°–91°C.

A mixture of isomeric aminobutanols (2-aminobutanol and 1-amino-2-butanol with an excess of the latter) may be also made in the following manner: 400 g of 26 per cent aqueous amonia solution (5.6 moles) were mixed with 21.6 of the mixture of butylene chlorohydrines (about 15 per cent 2-chloro-butanol-1 and 85 per cent 1-chloro-butanol-2 and left in a room temperature during 3–4 days. The mixture was then evaporated to dryness and a mixture of amonium chloride and 1-amino-2-butanol was obtained. The mixture was treated with 50 ml of a 40 per cent aqueous solution of sodium hydroxide. The aminobutanol was then separated by adding an excess of solid sodium hydroxide and by extracting with ether and/or benzene. The extract was dried over solid sodium hydroxide and distilled under reduced pressure. A fraction of 79°–81°C at 25 mm Hg was collected. The yield was 50–53 per cent based upon the mixture of butylene chlorhydrines used in the process.

What we claim is:

1. A process for the preparation of 2-aminobutanol comprising reacting 1,2-epoxybutane or butylene halogenhydrines with ammonia to form a mixture of isomeric aminobutanols, converting said mixture into 2-ethylaziridine by means of esterification with sulphuric acid, followed by reaction with alkali hydroxide; reacting 2-ethylaziridine with an aromatic carboxylic acid or with an anhydride of an orthobicarboxylic aromatic acid to produce an amide or a polyamide of 2-aminobutanol, and hydrolyzing with a mineral acid.

2. A process in accordance with claim 1 wherein said aromatic carboxylic acid is benzoic acid.

3. A process in accordance with claim 1 wherein said aromatic ortho-bicarboxylic anhydride is phthalic anhydride.

4. A process in accordance with claim 1 wherein the esterification with sulphuric acid is carried out in the presence of an azeotropic solvent with concurrent azeotropic distillation.

5. A process in accordance with claim 4 wherein toluene is used as an azeotropic solvent.

* * * * *